United States Patent [19]

Schneider et al.

[11] Patent Number: 5,136,624
[45] Date of Patent: Aug. 4, 1992

[54] PROCESS FOR INSPECTING MONOCRYSTALLINE MATERIAL FOR PRECIPITATION OF IMPURITIES

[75] Inventors: Jochen Schneider, Hamburg; Hans A. Graf, Berlin, both of Fed. Rep. of Germany

[73] Assignee: Deutsches Elektronen Synchrotron DESY, Hamburg, Fed. Rep. of Germany

[21] Appl. No.: 733,760

[22] Filed: Jul. 23, 1991

[30] Foreign Application Priority Data

Jul. 23, 1990 [DE] Fed. Rep. of Germany ....... 4023358

[51] Int. Cl.$^5$ .......................................... G01N 23/207
[52] U.S. Cl. ........................................ 378/73; 378/74
[58] Field of Search .................................... 378/73, 74

[56] References Cited

U.S. PATENT DOCUMENTS 4,217,493 8/1980 Li et al. ................................. 378/73
4,788,702 11/1988 Howe et al. ........................... 378/73

OTHER PUBLICATIONS

Iida, S., Sugiyama H., Sugita Y., and Kawata H. (Jun. 1988). Measurement and Analysis of the Static Debye--Waller Factor of Cz-Silicon with Small Oxygen Precipitates. *Japanese Journal of Applied Physics*, 27(8), 1081–1087.
James, R. W. (1965). *X-ray Crystallography*. New York: Wiley, pp. 56–70.
Bragg, W. L. (1975). *The Development of X-ray Analysis*. New York: Hafner, pp. 79–87.

*Primary Examiner*—Craig E. Church
*Attorney, Agent, or Firm*—Nils H. Ljungman & Associates

[57] ABSTRACT

In the manufacture and processing of monocrystalline material, it is important to be able to detect and measure deviations from the ideal crystal structure. Data are required on the density and average extent of impurity precipitations. The irradiation of discrete crystal areas with wave or particle beams, the determination of the intensity distribution of the beams scattered under Bragg conditions, and the determination of static Debye-Waller factors are to be performed automatically and universally, on different specimen thicknesses, with high resolution and flexibility regarding changes in wavelength. For this purpose, a variation of the angle of incidence of the beams on the diffracting lattice planes is performed, and the reflection factor is measured by means of a photon or particle detector, and the integral reflection factor Rint is determined. Pivoting the specimen around an axis which is perpendicular to the diffracting lattice planes leads to a variation of the specimen thickness. Rint is measured as a function of the specimen thickness. From the measured dependence, fitted to a theoretical function, the static Debye-Waller factor is determined, and when several diffraction orders are measured, the density or number and the average extent of the precipitations can also be determined. Important applications include the in situ determination of impurity precipitations in inspections of Si wafers, which can be mapped with high-sensitivity resolutions as a function of density and size of SiO2 precipitations, etc.

12 Claims, 4 Drawing Sheets

1. Determination of the Orientation of the Lattice Planes of the Monocrystalline Specimen

FIG. 4

2. Directing a Beam at the Lattice Planes of the Specimen

3. Varying the Incident Beam over a Plurality of Angles with respect to the Lattice Planes such that the Plane Defined by the Incident Beams and the Reflected Beams does not change relative to the Lattice Planes 4. Measuring the Intensity of the Reflected Beams for the Diffraction Order of Bragg Reflections over the Plurality of Angles for a Specimen Thickness 5. Integrating the Plurality of Measured Reflections over the Plurality of Angles to determine an Integral Reflection Factor for a Specimen Thickness 6. Varying the Effective Thickness of the Specimen by changing the Orientation of the Plane defined by the Incident Beam and the Reflected Beam relative to the Lattice Planes 7. Determining the Static Debye–Waller Factor for a Diffraction Order of Bragg Reflection by fitting a Function to the Integrated Reflection Factors and Specimen Thicknesses 8. Changing the Diffraction Order of Bragg Reflection 9. Evaluating the Debye–Waller Factors as a function of Diffraction Orders to determine the Extent of Impurities

PROCESS FOR INSPECTING MONOCRYSTALLINE MATERIAL FOR PRECIPITATION OF IMPURITIES

BACKGROUND OF THE INVENTION

1. Field of the Invention

This invention relates to a process for the inspection of monocrystalline material for the presence of precipitations of impurities, whereby discrete crystal regions are irradiated with wave or particle rays, the intensity distribution of rays diffracted under Bragg conditions is recorded, and a determination of the static Debye-Waller factor is made by fitting the recorded intensity values to a specified theoretical function.

2. Background of the Invention

Since the control and optimizing of the manufacture and processing of single crystals play an important role in many industrial applications, great significance is attached to processes which make it possible for the manufactured crystals to be inspected and the deviations from the ideal crystal structure detected. A typical use of such processes is the inspection of Silicon (Si) wafers which are to be reprocessed for use in the semiconductor and microelectronics industries.

Si wafers are generally in the form of monocrystalline discs with typical dimensions of approximately 0.4 mm thick and 200 mm in diameter. The wafers obtained, after the crystal drawing, contain an oxygen component on the order of magnitude of 10 ppm, with the exception of the active surface layer, approximately 20 mm thick, which is practically oxygen-free. During reprocessing the wafers are heated during tempering, whereby at approximately 700° C., the previously atomic oxygen tends to form $SiO_2$ molecules. The $SiO_2$ molecules can substitute for Si atoms in the crystal lattice, which causes local distortions of the lattice structures.

It has been shown that the distortion of the lattice has an attractive effect on additional $SiO_2$ molecules, which accumulate in the plane structure. In this manner, thin platelets of $SiO_2$ precipitations form, which causes stresses in the crystal. These precipitations also have the characteristic of gettering sinks. Gettering is the process by which existing defects are annihilated and impurities are removed. More specifically, intrinsic gettering occurs in Si crystals when the precipitations attract foreign atoms internally; in particular metal atoms such as Ag, Cu, etc., which originate from impurities in chemicals required during the manufacturing process for semiconductor elements, e.g. etching fluids. As a result of the intrinsic gettering, the yield during the manufacture of micro-electronic semiconductor components is significantly increased. A prerequisite of intrinsic gettering is that the intrinsic gettering layer is underneath the subsequently electrically active surface layer of the wafer. The gettering layer helps purify the electrically active surface layer.

The stresses caused by precipitations in the crystal lattice are reduced at the elevated temperatures of more than 1000° C., which elevated temperatures occur during the subsequent process stages, and result in stacking errors. The stacking errors cause extensive distortion fields, which extend into the oxygen-free surface layer. It is desirable, to "suck out" impurities from the surface layer and to fix the stacking errors in the lower crystal layers. Again, the intent is to purify the electrically active surface layer. It is therefore desirable to design the treatment processes for the wafer so that there is a uniform distribution and homogenization of the $SiO_2$ precipitations, to guarantee the most uniformly possible intrinsic gettering and thus to prevent disruptions of the electrically active surface layer.

Accordingly, there has long been a demand for a process by way of which the impurity precipitations can be made observable and measurable, in terms of density, size, and distribution, in the wafer. This is true in particular for a process which can be performed repeatedly in individual process steps or even in situ, i.e. during tempering of the wafer in a furnace.

The Japanese publication "Japanese Journal of Applied Physics, Volume 27, No. 8, June 1988, Pages 1081 to 1087 (S. Iida et al: Measurement and Analysis of the Static Debye-Waller Factor of Cz-Silicon with Small Oxygen Precipitates) discloses a method of the type described above, which is suitable for laboratory-scale tests on Si specimens for $SiO_2$ precipitations both of large extent and low density, and also for such microprecipitations whose dimensions are small in relation to the resolution of the X-ray diffraction intensity distribution recorded. The intensity distribution is thereby recorded photographically, and the blackening of the negative can be evaluated, for example, with a microdensitometer. For this purpose, specimens and sharply collimated beams must be oriented in a fixed manner, and the specimens and the negative to be exposed must be at the smallest possible distance from one another.

OBJECT OF THE INVENTION

Accordingly, the object of this invention is to create a process for such inspections which, as indicated above, can be used universally during the various steps of a manufacturing process, allows the use of different and large specimen thicknesses, makes possible a high resolution, is flexible with regard to changes in the wavelength of the radiation used, and which, in particular, meets the requirements for automation.

SUMMARY OF THE INVENTION

In the process according to the invention, the specimen to be tested is typically a crystal disc and is irradiated in Laue transillumination geometry. Thus, Bragg reflections occur on lattice planes of the lattice, which lattice planes are perpendicular to the crystal surface being irradiated. The orientation of the lattice planes of the crystal must be known or determined. Patents which involve the determination of crystal lattice plane orientation are U.S. Pat. No. 4,788,702 entitled "Orientation of Crystals" and U.S. Pat. No. 4,217,493 entitled "Hemispherical Laue Camera." The diffracted beam arrives at a photon detector, and the absolute reflection factor R can be determined in the manner of the prior art. The absolute reflection factor R is essentially the fraction of irradiation which is "reflected," a comparison of the incident intensity to the reflected intensity. Then the orientation of the crystal disc is varied, by rotating it around a first axis which is perpendicular to the diffraction plane defined by the incident and the diffracted beam. The reflection factor, as a function of the angle of rotation $\theta$ around the first axis, is recorded as the stored signals and leads to the Bragg reflection peak. An integration over the angle of rotation $\theta$ gives the integral reflection factor $$R_{int} = \Sigma R_i \times d\theta$$

Alternatively, the beam source could be moved about the specimen to achieve the same angle changes.

The value $R_{int}$ is now measured repeatedly in a series of measurements, whereby the effective specimen thickness is varied in succeeding measurements, i.e. the pathlength travelled by the beam in the crystal is changed. The variation of the effective specimen thickness results by pivoting the crystal disc around a second axis which is perpendicular to the lattice plane on which diffraction takes place. As a result of this variation of the pivot angle $\Phi$, the distance travelled by the wave or particle beam in the crystal changes, and accordingly the effective specimen thickness changes. But the angle of incidence of the beam to the lattice plane on which the beam is diffracted remains constant. In this manner, a measurement series with n measurements delivers a series of values $$R_{int}{}^j(\Phi_j), j=1,\ldots,n$$

as a function of the pivot angle positions $\Phi_j$ and accordingly of effective specimen thicknesses $d_j$. Alternatively, the beam source could be pivoted to achieve the same change in angle and effective change in specimen thickness.

The measured dependence $R_{int}{}^j(d_j)$ can be described by a theoretical expression $R_{int, theo}(d, E)$, which is given by the diffraction theory of Becker and Al Haddad (Dissertation: Al Haddad, University of Grenoble, 1989). The diffraction theory of Kato (N. Kato, Acta Cryst. (1980) 763, 770), as used by Iida (see also the above-referenced publication in Jp. J. Appl. Phys.), on the other hand, cannot be made to harmonize with the experimental tests. In both theories, the static Debye-Waller Factor E is included as a parameter; this parameter expresses deviations from the ideal crystal structure and is a function of the average displacement of the lattice atoms from the undisturbed lattice points in the crystal area observed. These known relationships, by measurements of the static Debye-Waller factor, make possible the calculation of density and extent of impurity precipitation in monocrystalline material. These calculations can be performed automatically, under the conditions specified by the invention.

In summary, one aspect of the present invention is a process for the inspection of monocrystalline material for precipitation of impurities, said process comprising the steps of:

a) determining the orientation of the lattice planes of the monocrystalline material;

b) directing an incident beam which is diffractable by the lattice planes of the monocrystalline material toward the monocrystalline material;

c) disposing said incident beam and the lattice planes at an angle relative to one another to provide a reflected beam for a diffraction order of Bragg reflection from the lattice planes;

d) orienting a detector, for measuring a Bragg reflection, and the lattice planes relative to one another to measure an intensity of said reflected beam of step c) for said diffraction order of Bragg reflection from the lattice planes;

e) varying said angle of said incident beam over a plurality of angles with respect to the lattice planes in a plane, said plane defined by said plurality of incident beams and a plurality of reflected beams all lying in said plane, said plane being disposed to maintain substantially a sole orientation relative to the lattice planes;

f) varying the orientation of said detector in substantially said plane between said detector and the lattice planes over said plurality of angles so that said detector measures said plurality of reflected beams of step e) to provide a plurality of measured reflections;

g) integrating said plurality of measured reflections over said plurality of angles of the incident beam with respect to the lattice plane to determine an integral reflection factor;

h) varying an effective thickness of the monocrystalline material relative to the path of the incident and reflected beams by changing the orientation of said plane defined by said plurality of incident beams and said plurality of reflected beams with respect to the lattice planes, then repeating steps c) through g);

i) determining a Debye-Waller factor by fitting to a specified theoretical function, in which, with said Debye-Waller factor as a parameter, said integral reflection factor is calculated as a function of said effective thickness of the monocrystalline material;

j) performing at least one additional series of measurements, in which the steps c) through i) are repeated with at least one other diffraction order, and at least one other Debye-Waller factor is determined; and k) evaluating said Debye-Waller factors as a function of said diffraction orders to determine an extent of precipitated impurities in the monocrystalline material.

Discussions of intensities of X-ray spectra and reflection are in the book by James, R. W. (1965), *X-ray Crystallography*, New York: Wiley; pp. 56–70; and the book by Bragg, W. L. (1975), *The Development of X-ray Analysis*, New York: Hafner, pp. 79–87.

BRIEF DESCRIPTION OF THE DRAWINGS

The invention is explained in greater detail below with reference to the accompanying drawings, in which:

FIG. 4: shows a flow diagram of the process.

DESCRIPTION OF THE PREFERRED EMBODIMENTS

Figure 1:
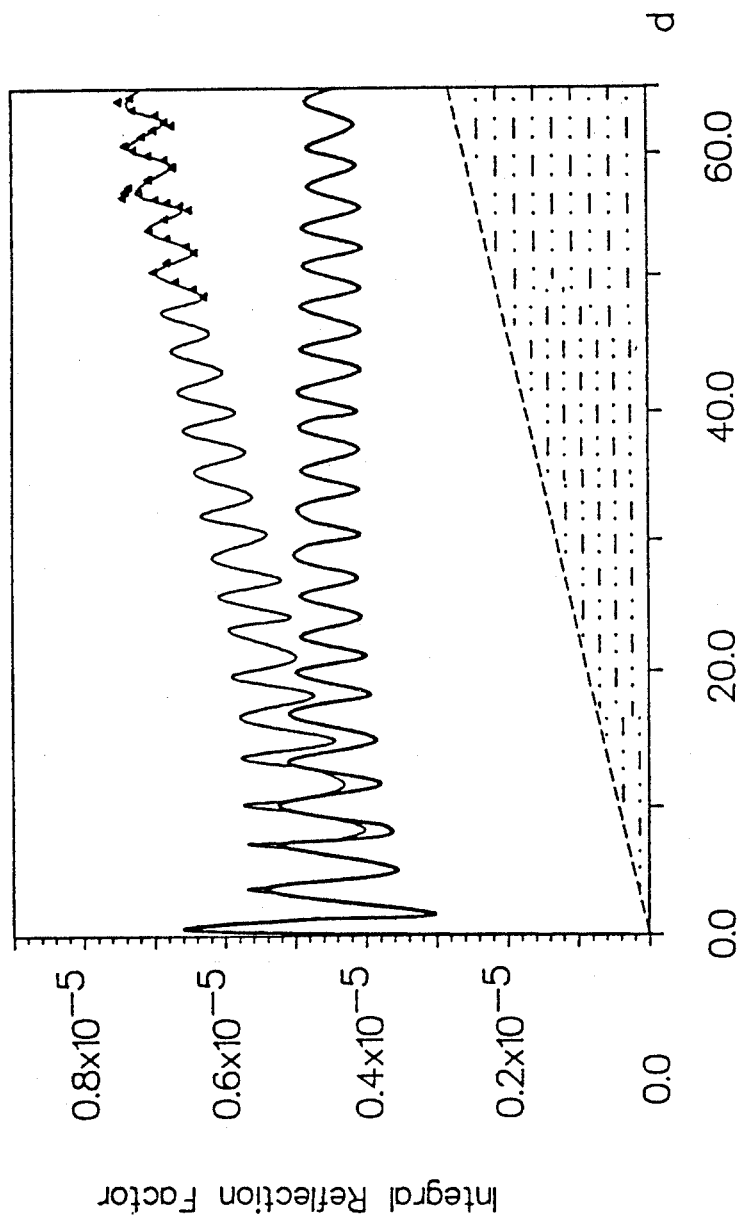
FIG. 1: shows the integral reflection factor as a function of the specimen thickness.

The measurements performed in connection with this invention show that impurity precipitations have a significant influence on the reflection factor, which is manifested as a linear increase of $R_{int}$ with the effective specimen thickness; the integral reflection factor can thereby reach values which are significantly higher than those of an undisturbed, ideal crystal, for which ideal crystal $R_{int}$ exhibits only an oscillatory behavior (known as periodic oscillations or Pendelloesung oscillations), but no linear increase with the specimen thickness. This is shown in FIG. 1, which illustrates the integral absolute reflection factor as a function of the specimen thickness for a perfect crystal (thick line) and an actual Si crystal disrupted by $SiO_2$ precipitations (thin line and measurement points). The integral absolute reflection factor, of an actual Si crystal disrupted by $SiO_2$ precipitations, is the sum of a component of the perfect crystal and a component which increases with the specimen thickness as a result of impurity precipitations (dashed line).

Figure 2:
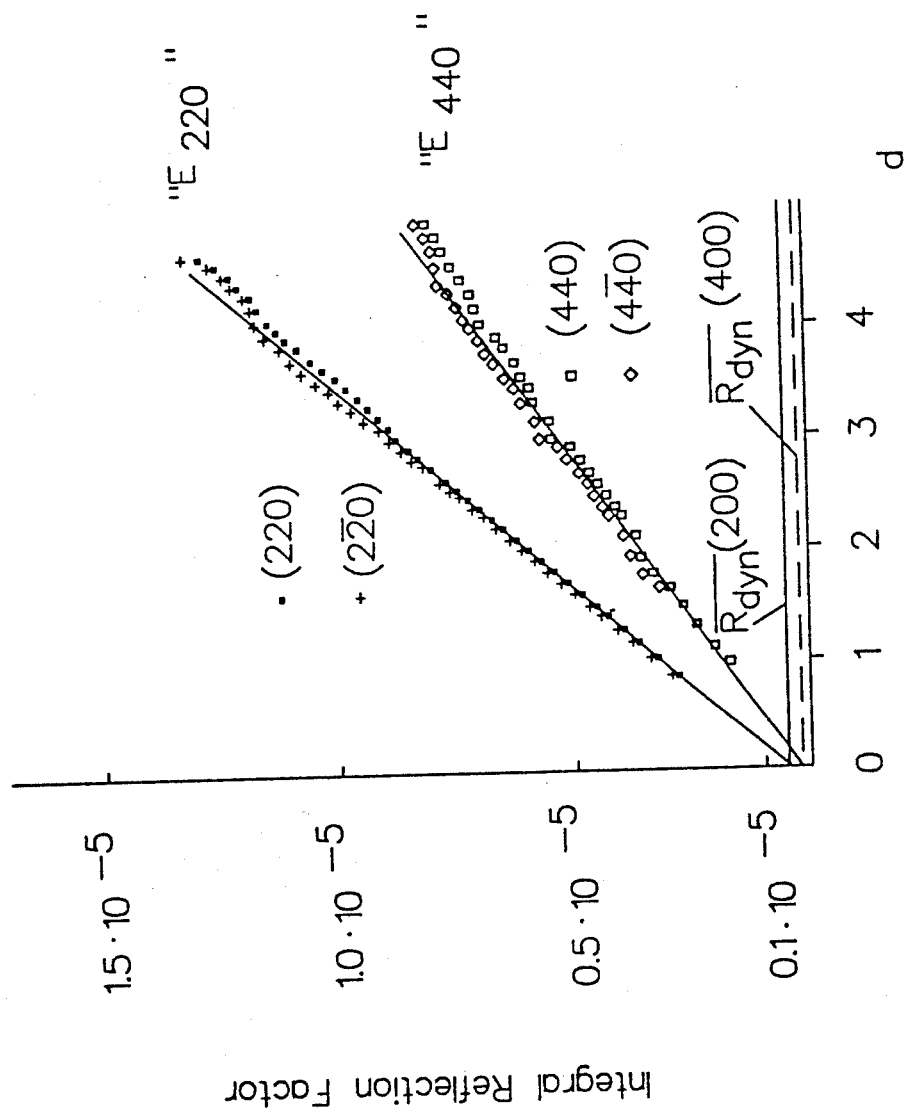
FIG. 2: shows the integral reflection factor as a function of the specimen thickness, as in FIG. 1, but on a different scale and for a different crystal.

FIG. 2 shows the sharp increase of the reflection factor with the specimen thickness, which thereby reaches values which are significantly higher than those of an undisturbed crystal whose average reflection factor is represented by the constant straight lines in the lower portion of FIG. 2. This sensitive dependence of the reflection factor on crystal disruptions, by a fitting to the theoretical expression $$R_{int,\ theo}(d,\ E)$$

to the measurement series
$$R_{int}^j(d_j),$$

makes possible a very precise determination of the static Debye-Waller factor. From the measurement of the Debye-Waller factor for at least two diffraction orders, it is possible using methods of the prior art to obtain the density of precipitations, i.e. the number of precipitations and their average extent. For this purpose, the Debye-Waller factors, e.g. of the 220 reflections and the next higher 440 reflections, are measured in succession, and the corresponding results $E_{220}$ and $E_{440}$ are used for the calculation. FIG. 2 shows the integral absolute reflection factor for the 220 reflection and the 440 reflection, from which by fitting to the theoretical function, the corresponding Debye-Waller factors $E_{220}$ and $E_{440}$ can be determined.

Figure 3:
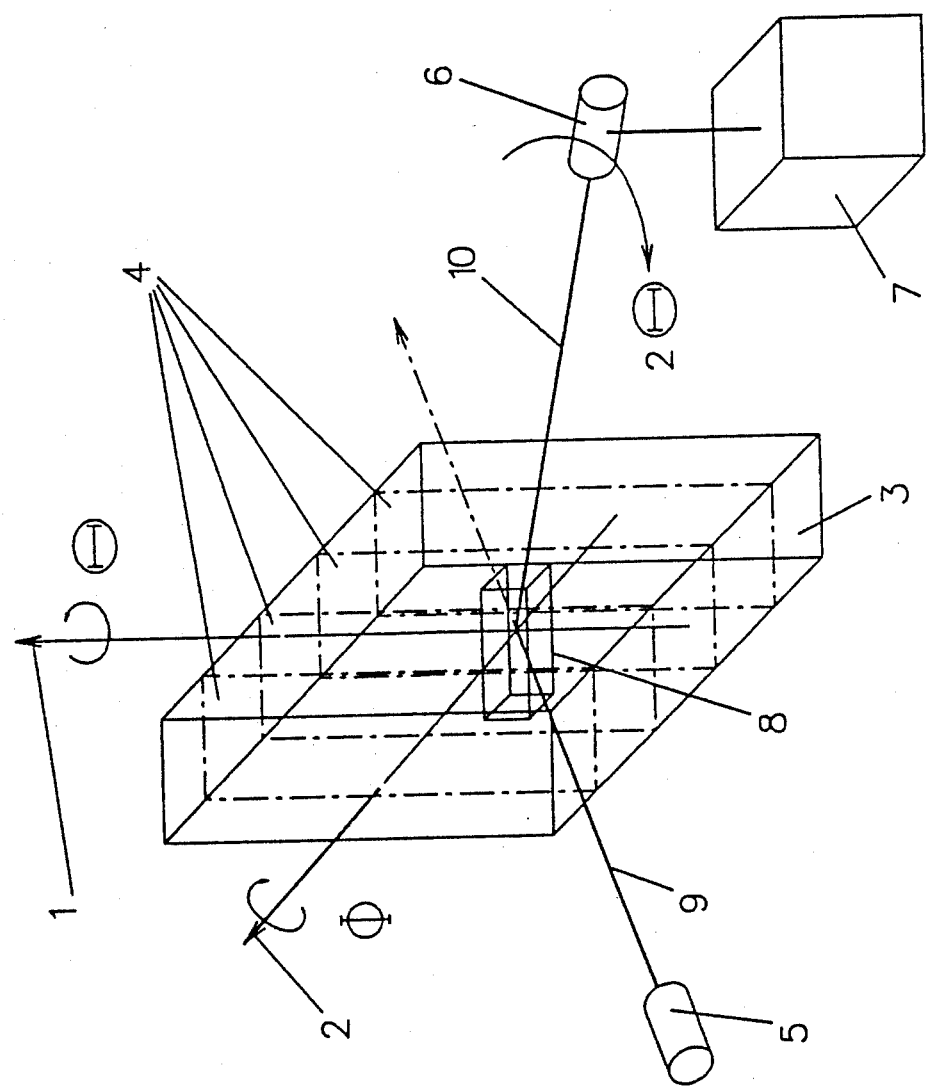
FIG. 3: shows a schematic diagram of an apparatus for the performance of the process.

The crystal specimen designated 3 in FIG. 3 contains the lattice plane family 4. The lattice plane family 4 is oriented perpendicular to the crystal surface. Diffraction takes place on the lattice plane family 4. The thickness of the crystal discs to be inspected should be approximately in the range of 0.3 mm to 10 mm for silicon, whereby the maximum thickness is determined by the average free distance of the photon or particle beams.

The beam source 5 generates, for example, an X-ray beam 9 which falls on a surface element of the specimen 3. In the preferred embodiment, the wavelength of the X-rays should be in the range of 0.02 to 0.003 nm (corresponding to photon energies from 50 to 450 keV). The X-ray sources used can thereby be all devices of the prior art, such as X-ray tubes or even strongly radioactive gamma preparations. The use of synchrotron radiation is particularly advantageous, as explained below.

The Bragg scattering of the incident ray 9 on the lattice plane 4 generates a diffracted beam 10 which with the high photon energies used, exits at a low angle to the incoming beam. A photon detector 6 is used to detect the X-rays. All photon detectors of the prior art which have a sufficiently high detection efficiency at high photon energies can be used for this purpose, e.g. NaI scintillation counters or Ge semiconductor detectors. The electrical output signals are transported to a processing unit 7 and are recorded there in an electronic memory.

For the measurement of the integral absolute reflection factor, the orientation of the specimen 3 is varied. For this purpose, the crystal disc is rotated around the axis 1, which is perpendicular to the diffraction plane defined by the incident beam and the diffracted beam. The angle between the incident beam and the diffracting lattice plane 4 is thereby varied.

By measurement of the reflection factor in a series of settings of the angle of rotation $\theta$ around the axis 1, a reflection peak whose position is determined by the Bragg Equation is obtained as a function of $\theta$. The integral reflection factor $R_{int}$ results from integration of the measurements over the angular rotation settings $\theta$. The integration can be performed in a different manner, e.g. by adding up the individual measurements stored digitally in the processing unit; likewise, the integration can be performed with continuous and uniform variation of the angle of rotation $\theta$ by accumulation or temporal integration of the measurement results.

In the next step, the effective specimen thickness of the crystal disc is varied by pivoting the specimen 3 around the axis 2. During rotation around the axis 2, the incident angle of the radiation to the lattice plane remains constant, while the distance travelled in the crystal disc changes, and thus the effective specimen thickness at $1/\cos(\Phi)$ changes ($\Phi = 0$ for perpendicular incidence) and can be adjusted continuously.

In repeated measurements of $R_{int}$ at successive settings $\Phi_j$ of the pivot angle, the setting $\Phi_j$ and the corresponding measurement $R_{int}^j$ are always recorded. In this manner, with n successive settings $\Phi_j$, the result is a series of measurements
$$R_{int}^j(\Phi_j),\ j = 1, \ldots, n$$

or an equivalent series of measurements as a function of the specimen thickness $R_{int}^j(d_j)$, whereby the measurement series is stored in the processing unit.

The integral absolute reflection factor measured as a function of the specimen thickness is then compared to the theoretical expectation $R_{int,\ theo}(d,E)$ to determine, as a result, the static Debye-Waller factor.

The processing of the measurement results, by fitting to the theoretical function, can either be done by calling up the results in an external computational device, or in a computational unit integrated into the processing unit 7. The fitting to the theoretical function is thereby performed, as a rule, by numerical variation of the parameter E being fitted with one of the current fitting processes, e.g. least squares fitting or chi$^2$ minimization.

The result of the fitting for the static Debye-Waller factor E or a value which is clearly a function of it, e.g. the Debye-Waller parameter L (defined as $E = \exp(-L)$), represents the measurement resulting from the process according to the invention, from which, with a combination of several diffraction orders, the density and extent of precipitated impurities can be derived.

The flow chart in FIG. 4 helps illustrate the process with the following steps:

1. Determination of the Orientation of the Lattice Planes of the Monocrystalline Specimen. The lattice plane orientation is determined by a separate process or is known based on the manufacture of the crystal.

2. Directing a Beam at the Lattice Planes of the Specimen. The source of a photon or particle beam which is diffractable by the crystal is oriented to direct its beam at the lattice planes of the specimen.

3. Varying the Incident Beam over a Plurality of Angles with respect to the Lattice Planes such that the Plane Defined by the Incident Beams and the Reflected Beams does not change relative to the Lattice Planes. This is accomplished either by rotating the specimen about axis 1 (FIG. 3) to change the angle or changing the position of the beam source to change the angle. When the specimen is rotated about axis 1 the plane formed by the incident and reflected beams does not change its orientation relative to the lattice planes.

4. Measuring the Intensity of the Reflected Beams for a Diffraction Order of Bragg Reflections over the Plurality of Angles for a Specimen Thickness. The detector has to be moved as the incident angle varies in order to measure the intensity of the beam diffracted as a Bragg reflection. This is done for only a single order of diffraction.

5. Integrating the Plurality of Measured Reflections over the Plurality of Angles to determine an Integral Reflection Factor for a Specimen Thickness. The measured reflections are integrated over the plurality of angles to determine an integral reflection factor for a single specimen thickness and a single diffraction order.

6. Varying the Effective Thickness of the Specimen by changing the Orientation of the Plane defined by the Incident Beam and the Reflected Beam relative to the Lattice Planes. The thickness of the specimen through which the incident and reflected beams pass can be varied by rotating the specimen about axis 2. The beam source can also be moved to vary the specimen thickness. At this point, steps 3-6 above are repeated, so that an integrated reflection factor is determined for each of the specimen thicknesses for which measurements are made. The series of integrated reflection factors and corresponding thicknesses are for a single diffraction order.

7. Determining the Static Debye-Waller Factor for a Diffraction Order of Bragg Reflection by fitting a Function to the Integrated Reflection Factors and Specimen Thicknesses. A single static Debye-Waller factor is determined from the series of integrated reflection factors and corresponding thicknesses which are all for a single diffraction order.

8. Changing the Defraction Order of Bragg Reflection. Now steps 3-7 above are repeated for another diffraction order, and another static Debye-Waller factor is determined.

9. Evaluating the Debye-Waller Factors as a function of Diffraction Orders to determine the Extent of Impurities. The combination of static Debye-Waller factors are used to determine the density and extent of precipitated impurities.

It should be noted that, to this extent, it is a question of a local measurement process, i.e. with the irradiation of a small crystal surface element, the measurement results are obtained for a discrete area of the crystal disc. If a high-sensitivity resolution inspection is desired, the crystal disc can be scanned by relative translation in relation to the wave or particle beam, i.e. there can also be a high-sensitivity resolution determination of the distribution of impurity precipitations, and the crystal disc can be mapped. That is, more than one area of the crystal can be examined by the process.

In one particularly advantageous embodiment of the invention, as noted above, synchrotron radiation and an energy dispersive detector are used. The continuous spectrum of the synchrotron radiation makes it possible to satisfy the Bragg Equation for several diffraction orders with a discrete crystal position. To simplify the measurement, the process according to the invention makes it possible to measure the integral absolute reflection factor for several diffraction orders simultaneously.

Several advantageous characteristics of the process according to the invention are apparent. The process according to the invention makes possible a determination of the static Debye-Waller factor with high-sensitivity resolution, i.e. a mapping of the monocrystalline wafer. The measurement process can be conducted rapidly since, for example, with sufficiently strong X-ray sources, the individual measurements can be performed very quickly. One significant advantage is also the use of low wavelengths, since with short-wave radiation, the uncertainties caused by absorption effects in the crystal on the one hand and in the walls of the surrounding apparatus on the other hand are negligible. Therefore even thick specimens can be inspected, or measurements can be taken during individual operational steps in situ, e.g. on crystals which are being tempered inside a furnace; and through the use of beams having very short wavelengths, there is no significant interference caused by the walls of the furnace.

One aspect of the invention resides broadly in the process for the inspection of monocrystalline material for precipitations of impurities, whereby an irradiation of discrete crystal areas with wave or particle beams, a recording of the intensity distribution of beams diffracted under Bragg conditions and a determination of the static Debye-Waller factor are conducted with a fitting of the intensity values recorded to a specified theoretical function, characterized by the automated steps listed below with the indicated details:

A) 1) Inspection of a first discrete crystal area of a specimen in the shape of a disc or platelet 3, by:

i) Measurement of the absolute reflection factor in a first diffraction order with Bragg reflection on lattice planes 4 of the crystal lattice which are perpendicular to the crystal surface, by means of a photon or particle detector 6;

ii) Rotation of the specimen 3 around a first axis 1 which runs perpendicular to the diffraction plane which is defined by the incident beam and the diffracted beam, for variation of the beam/specimen 3 orientation;

iii) Storage of the signals emitted by the photon or particle detector 6 for the measured reflection factor as a function of the angle of rotation of the specimen 3 around its first axis 1;

iv) Integration of these measurements over the angle of rotation for the determination of the integral reflection factor $R_{int}$;

v) Variation of the effective thickness of the specimen 3 by pivoting the specimen 3 around a second axis 2, which is perpendicular to the lattice plane 4, on which diffraction takes place, with repetition of the operations indicated in i) to iv);

vi) Determination and storage of the integral reflection factor for a number j of settings of the pivot angle as a series of measurements $R_{int}^j$ as a function of the effective thickness of the specimen 3;

vii) Determination of the first static Debye-Waller factor ($E_{220}$) by fitting to the specified theoretical function, in which with E as a parameter, the integral reflection factor is calculated as a function of the thickness of the specimen 3, in the sequence of the recorded measurements of $R_{int}^j$;

B) Performance of at least one additional series of measurements, in which the process steps A 1) i) to A 1) vii) are repeated as A 1+n) i) to A 1+n) vii) with another diffraction order, and at least one additional Debye-Waller factor ($E_{440}$, ...) is determined;

C) Evaluation of the investigations performed in the individual series A) to B) with the static Debye-Waller factor as a function of the diffraction order with reference to the density and the average extent of precipitated impurities.

Another aspect of the invention is characterized by the additional steps indicated below:

D) Investigation of at least one additional discrete crystal area by high-sensitivity resolution repetition of the process steps A) to C) on the specimen 3;

E) Mapping of the high-sensitivity resolution data measured on the specimen 3 in relation to the density and average extent of precipitated impurities in the crystal lattice of the monocrystalline material.

Yet another aspect of the invention is characterized by the fact that for the irradiation of the specimen 3, X-ray radiation in the wavelength range of about 0.02 nm to 0.003 nm is used, corresponding to photon energies of about 50 keV to 450 keV.

A further aspect of the invention is characterized by the fact that for the irradiation of the specimen 3, synchrotron radiation is used, and there is an energy dispersive detection of the dispersed radiation.

All, or substantially all, of the components and methods of the various embodiments may be used with at least one embodiment or all of the embodiments, if any, described herein.

All of the patents, patent applications and publications recited herein, if any, are hereby incorporated by reference as if set forth in their entirety herein.

The details in the patents, patent applications and publications may be considered to be incorporable, at applicant's option, into the claims during prosecution as further limitations in the claims to patentably distinguish any amended claims from any applied prior art.

The invention as described hereinabove in the context of the preferred embodiments is not to be taken as limited to all of the provided details thereof, since modifications and variations thereof may be made without departing from the spirit and scope of the invention.

What is claimed is:

1. Process for the inspection of monocrystalline material for precipitation of impurities, said process comprising the steps of:
    a) determining the orientation of the lattice planes of the monocrystalline material;
    b) directing an incident beam which is diffractable by the lattice planes of the monocrystalline material toward the monocrystalline material;
    c) disposing said incident beam and the lattice planes at an angle relative to one another to provide a reflected beam for a diffraction order of Bragg reflection from the lattice planes;
    d) orienting a detector, for measuring a Bragg reflection, and the lattice planes relative to one another to measure an intensity of said reflected beam of step c) for said diffraction order of Bragg reflection from the lattice planes;
    e) varying said angle of said incident beam over a plurality of angles with respect to the lattice planes in a plane, said plane defined by said plurality of incident beams and a plurality of reflected beams all lying in said plane, said plane being disposed to maintain substantially a sole orientation relative to the lattice planes;
    f) varying the orientation of said detector in substantially said plane between said detector and the lattice planes over said plurality of angles so that said detector measures said plurality of reflected beams of step e) to provide a plurality of measured reflections;
    g) integrating said plurality of measured reflections over said plurality of angles of the incident beam with respect to the lattice plane to determine an integral reflection factor;
    h) varying an effective thickness of the monocrystalline material relative to the path of the incident and reflected beams b changing the orientation of said plane defined by said plurality of incident beams and said plurality of reflected beams with respect to the lattice planes, then repeating steps c) through g);
    i) determining a Debye-Waller factor by fitting to a specified theoretical function, in which, with said Debye-Waller factor as a parameter, said integral reflection factor is calculated as a function of said effective thickness of the monocrystalline material;
    j) performing at least one additional series of measurements, in which the steps c) through i) are repeated with at least one other diffraction order, and at least one other Debye-Waller factor is determined; and
    k) evaluating said Debye-Waller factors as a function of said diffraction orders to determine an extent of precipitated impurities in the monocrystalline material.

2. Process according to claim 1, wherein steps a) through k) are repeated for at least one additional discrete crystal area of the monocrystalline material and mapping the data measured on the monocrystalline material in relation to the extent of precipitated impurities in the monocrystalline material.

3. Process according to claim 2, wherein said beam comprises X-ray radiation in the wavelength range of about 0.02 nm to 0.003 nm, corresponding to photon energies of about 50 keV to 450 keV.

4. Process according to claim 2, wherein said beam comprises synchrotron radiation, and said detector comprises a detector for energy dispersive detection of the dispersed radiation.

5. Process according to claim 3, wherein said lattice planes of the monocrystalline material being perpendicular to at least one surface of the monocrystalline material.

6. Process according to claim 5, wherein said varying of said angle of the incident beam over a plurality of angles with respect to the lattice planes in a plane, is accomplished by rotating the monocrystalline material about an axis being parallel to said lattice planes.

7. Process according to claim 6, wherein said axis is parallel to said at least one surface of the monocrystalline material being perpendicular to said lattice planes of the monocrystalline material.

8. Process according to claim 7, wherein said varying of said effective thickness of the monocrystalline material relative to the path of the incident and reflected beams is accomplished by rotating the monocrystalline material about an axis being perpendicular to said lattice planes and intersecting said axis being parallel to said lattice planes.

9. A Process for the inspection of monocrystalline material for precipitations of impurities, comprising:
    A) 1) Inspection of a first discrete crystal area of a monocrystalline specimen, said area being in the shape of a disc or platelet, by:
        a) Measurement of an absolute reflection factor in a first diffraction order of Bragg reflection by lattice planes of the specimen, said lattice planes being perpendicular to the specimen surface, said measurement by means of an incident radiation beam and a photon or particle detector;
        b) Rotation of the specimen around a first axis which runs perpendicular to a diffraction plane, said diffraction plane being defined by said incident beam and a diffracted beam, said rotation for variation of the beam/specimen orientation;

c) Movement of said detector within said diffraction plane, to receive the diffracted beam and create a signal;

d) Storage of said signals emitted by said photon or particle detector of said measured reflection factor as a function of an angle of rotation of the specimen around said first axis;

e) Integration of said measurements over said angle of rotation for the determination of the integral reflection factor $R_{int}$;

f) Variation of an effective thickness of the specimen by pivoting the specimen around a second axis at an angle, said second axis being perpendicular to said lattice planes, with repetition of the operations indicated in a) to e);

g) Determination and storage of said integral reflection factor for a number j of settings of said pivot angle as a series of measurements $R_{int}^j$ as a function of said effective thickness of the specimen; and h) Determination of the first static Debye-Waller factor ($E_{220}$) by fitting to a specified theoretical function, in said function, with E as a parameter, said integral reflection factor is calculated as a function of said thickness of the specimen, in the sequence of the recorded measurements of $R_{int}^j$;

B) Performance of at least one additional series of measurements, in said series of measurements steps A) 1) a) to A) 1) h) are repeated as A) 1+n) a) to A) 1+n) h) with another diffraction order, and at least one additional Debye-Waller factor ($E_{440}, \ldots$) being determined; and C) Evaluation of the investigations performed in the individual series A) to B) with the static Debye-Waller factor as a function of said diffraction order to determine the density and the average extent of precipitated impurities in said area of the specimen.

10. The process of claim 9, further comprising:

D) Inspection of at least one additional discrete crystal area of the specimen, by repetition of steps A) to C) on the specimen to determine ; and E) Mapping of the density and average extent of precipitated impurities in the crystal lattice of the monocrystalline material for said discrete areas.

11. The process of claim 10, wherein said radiation beam comprises X-ray radiation in the wavelength range of about 0.02 nm to 0.003 nm is used, corresponding to photon energies of about 50 keV to 450 keV.

12. The process of claim 10, wherein said radiation comprises synchrotron radiation, and said detector comprises a detector for energy dispersive detection of the dispersed radiation.

* * * * *